United States Patent [19]

Ask et al.

[11] Patent Number: 4,732,160
[45] Date of Patent: Mar. 22, 1988

[54] METHOD OF FLOW MEASUREMENT AND FLOW METER

[76] Inventors: Per Ask, Konsistoriegatan 17 A, S-582 34 Linköping; Anders Engberg, Heidenstamsgatan 104, S-582 49 Linköping; Anders Spångberg, Heidenstamsgatan 24, S-582 49 Linköping; Åke Öberg, Ugglebovägen 79, S-590 60 Ljungsbro, all of Sweden

[21] Appl. No.: 680,251

[22] PCT Filed: Mar. 23, 1984

[86] PCT No.: PCT/SE84/00106
§ 371 Date: Nov. 26, 1984
§ 102(e) Date: Nov. 26, 1984

[87] PCT Pub. No.: WO84/03824
PCT Pub. Date: Oct. 11, 1984

[30] Foreign Application Priority Data

Mar. 30, 1983 [SE] Sweden ................................ 8301766

[51] Int. Cl.$^4$ .............................................. A61B 5/00
[52] U.S. Cl. ...................................... 128/760; 73/861; 177/4; 177/211
[58] Field of Search ................... 128/760; 73/861, 296; 177/210 R, 211, 210 FP, 4

[56] References Cited

U.S. PATENT DOCUMENTS

| 2,859,956 | 11/1958 | Meriam | 177/4 |
| 3,056,293 | 10/1962 | Ofner | 73/198 |
| 3,269,175 | 3/1964 | Sprosty | 73/DIG. 4 |
| 3,988,933 | 11/1976 | Fletcher et al. | 177/1 |

FOREIGN PATENT DOCUMENTS 430985 11/1933 United Kingdom .

OTHER PUBLICATIONS

Derwent's Abstract No. K1202 C/42 SU 718 709, Feb. 1980.

Primary Examiner—Edward M. Coven
Assistant Examiner—Randy Citrin
Attorney, Agent, or Firm—Brumbaugh, Graves, Donohue & Raymond

[57] ABSTRACT

A method of urine flow measurement where liquid in the form of a free-fall jet is collected in a collecting vessel and the vertical force produced by the collecting vessel on a measuring device, for example a scale or the like, is sensed, and the change in time of said force is utilized for obtaining a measure of the flow corresponding to the jet. The method is especially characterized in that the effect of the impulse of the jet on the sensed force is eliminated by deflecting the vertical flow constituted by the jet to a substantially horizontal flow by a rotating device before the liquid is caused to contact the vessel. The invention also relates to a flow meter.

15 Claims, 10 Drawing Figures

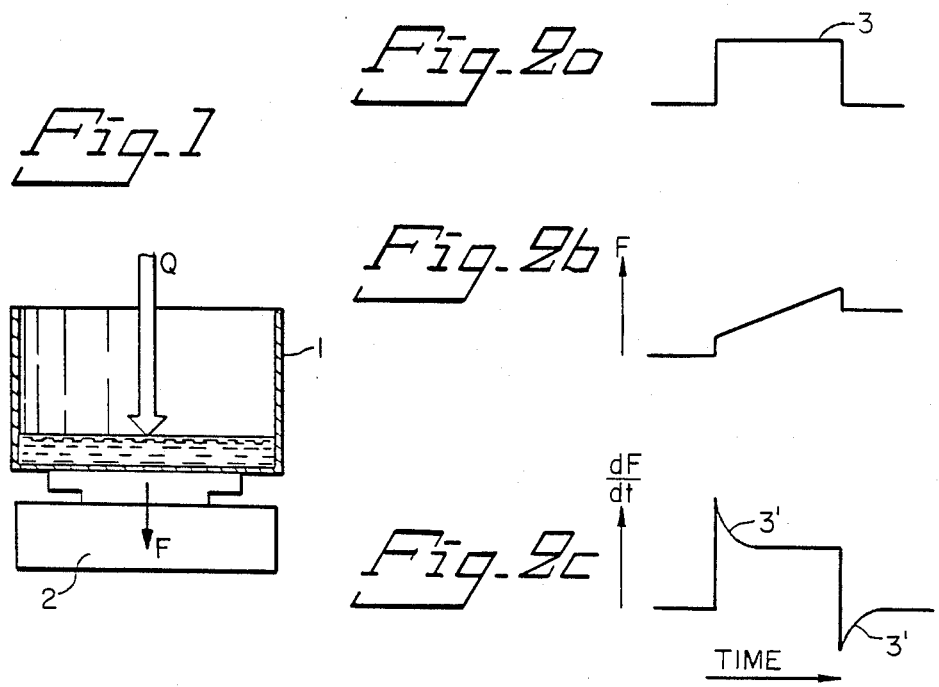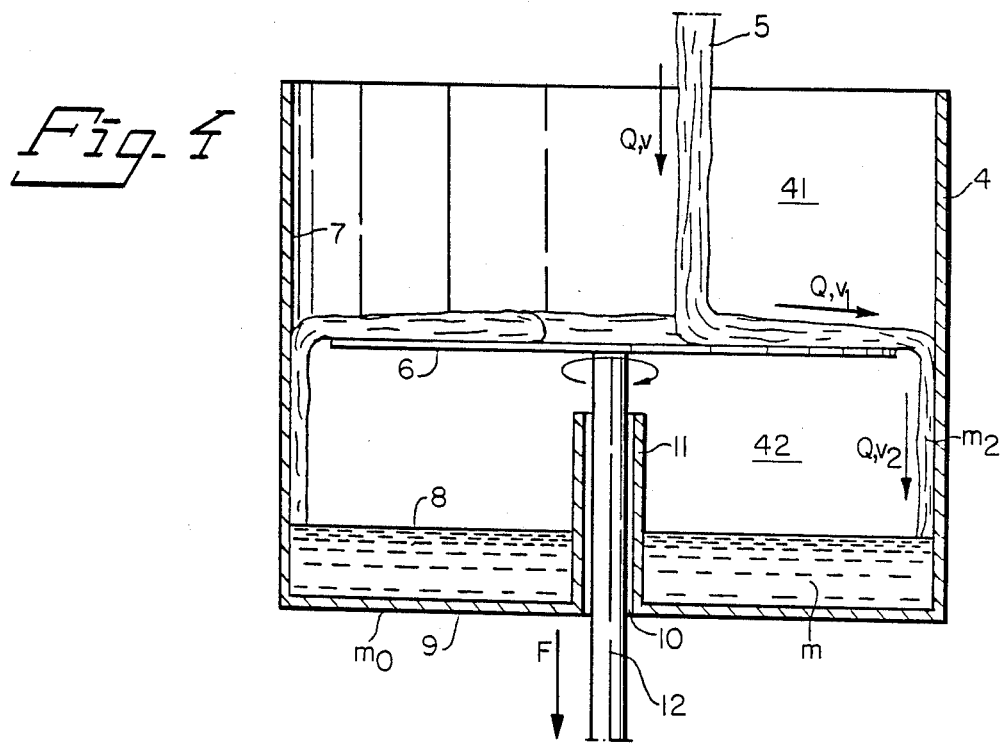

METHOD OF FLOW MEASUREMENT AND FLOW METER

BACKGROUND OF THE INVENTION

This invention relates to a method for urine flow measurement wherein liquid in the form of a free-falling jet is collected in a collecting vessel, and the weight of the vessel as a vertically acting force is continuously sensed and utilized for yielding a measure of the flow.

The invention also relates to a flow meter for carrying out the method.

During examination of the function of the lower ureters of a human being, the measurement of the urine flow as a function of the time, is the objective examination method which offers the greatest potential possibilities for obtaining copious information. Based upon the urine flow and the hydrostatic pressure in the bladder of a person, the elastic properties of the urethra determining the urine flow can be obtained. It is a prerequisite, however, that this flow and pressure can be measured accurately. Known urine flow meters, however, yield serious errors in measurement.

In a usual method of flow measurement, a scale with a collecting vessel is used. The force, F, recorded by such a scale is given by the equation $$F = m_o g + gp \int_o^t Q dt + vQ \qquad (1)$$

where $m_o$ is the initial mass of the vessel, g is the acceleration of gravity, p is the density of the urine, t is the time, Q the volume flow for the urine, and v the corresponding flow rate. The integral term in equation 1 corresponds to the volume. The last term in the expression is the reaction force due to the kinetic energy of the urine jet.

In order to receive an output signal corresponding to the flow, the first derivative of the force signal is determined, whereby $$\frac{dF}{dt} = gpQ + \frac{dv}{dt} Q + v \frac{dQ}{dt} \qquad (2)$$

The first term of the derivative, i.e. gpQ, is proportional to the desired flow. The remaining two terms are false signals occurring as a result of flow variations. The effect of these false terms can be illustrated by the recorded flow at an imagined pulse shaped uring flow. When the flow starts and ceases, due to said reaction force in principle infinitely large derivative terms are obtained which yield large overshoots in the measured valves. These overshoots can be filtered out, but the system then receives a very slow response.

Some of the problems with the kinetic energy of the urine jet can be overcome by collecting the urine in a funnel intended to take up the reaction force. The funnel, however, introduces a problem which potentially is still more serious, viz. a variable delay of the flow. This delay depends on where the urine jet meets the funnel. When a jet with constant flow is caused to oscillate over the funnel, this variable delay gives rise to a false variation in the flow which is recorded by the equipment.

In a known type of flow meter the flow is related to the effect which is required to accelerate the liquid to the circumferential speed of a rotating plate. The urine, however, here is collected by a funnel, and therefore the method and meter are afflicted with the errors in measurement involved therewith. When the urine jet is caused to directly meet the rotating plate, the reaction force of the jet affects the necessary effect for maintaining the rotation of the plate constant.

SUMMARY OF THE INVENTION

The present invention relates to a flow meter substantially designed according to the aforesaid scale principle. In the flow meter according to the invention, the problems referred to above have been substantially eliminated so that the flow can be measured with very high accuracy.

The present invention, thus, relates to a method of urine flow measurement where liquid in the form of a free-falling jet is collected in a collecting vessel, and the vertical force produced by the collecting vessel on a measuring member, for example a scale or the like, is sensed. The change in time of said force is utilized to determine the flow corresponding to the jet.

The method is especially characterized in that the influence of the impulse of the jet on the sensed force is eliminated by deflecting the vertical flow constituted by the jet to a substantially horizontal flow by means of a rotating device before the urine is caused to contact the vessel.

The invention also relates to a flow meter for urine flow measurement, wherein urine in the form of a free-falling jet is continuously collected in a collecting vessel, and wherein means, for example a scale or the like, are provided for sensing a vertical force produced by the vessel. The change in time of said force is intended to be utilized for determining the flow corresponding to the jet.

The flow meter according to the invention is especially characterized in that it comprises a rotary device free from said vessel, by means of which device the vertical flow constituted by the jet is deflected to a substantially horizontal flow prior to the urine striking the wall or base of the vessel, so that the influence of the impulse of the jet on the sensed force is eliminated.

BRIEF DESCRIPTION OF THE DRAWINGS

The invention is described in greater detail in the following, with reference to an embodiment and the accompanying drawings, in which;

FIG. 1 schematically shows a known arrangement for flow measurement involving weighing, FIGS. 2a–c schematically show by way of curves real flow, recorded volume and recorded flow at a known flow meter substantially according to FIG. 1.

FIG. 3 respectively, shows recorded flow as a function of the time, where the flow is maintained constant while the liquid jet is caused to oscillate over a collecting funnel comprised in the flow meter, FIG. 4 is a schematic vertical section through a part of an apparatus according to the invention.

In FIG. 1 the numeral 1 designates a collecting vessel, and 2 is a scale, on which the vessel 1 is placed. An arrangement of this known type involves errors in measurement as referred to above. In FIG. 2c overshoots 3' from the actual pulse shape flow 3, FIG. 2a, are observed as a result of the jet impulse. In FIG. 3 pulsations in the recorded flow at the use of a funnel are shown, through which funnel the liquid is caused to pass prior to the arrival at the collecting vessel at a flow meter according to FIG. 1, which pulsations are obtained from liquid jet oscillating over the funnel.

Figure 5:
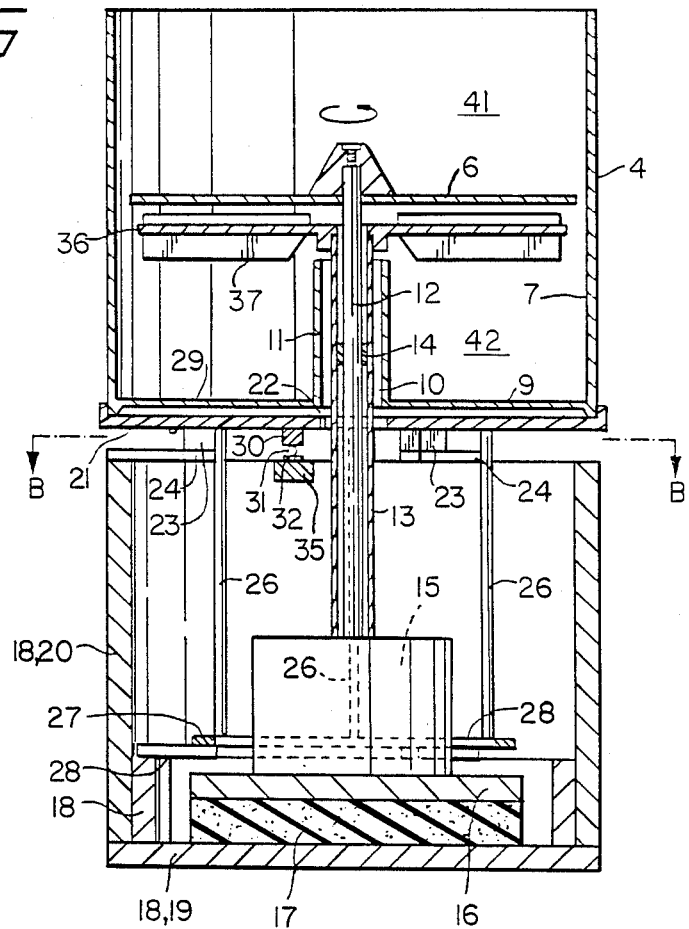
FIG. 5 is a schematic vertical central section A—A according to FIG. 6 through an embodiment of an apparatus according to the invention.

In the embodiment of an apparatus according to the invention shown partially and schematically in FIG. 4 the numeral 4 designates a collecting vessel, to which a liquid flow in the form of a jet 5 is intended to enter. 6 designates a rotary, substantially horizontal and preferably circular disc located in, but not in contact with the vessel 4 and preferably substantially adjoining the inner wall 7 of the vessel. The rotary disc 6 substantially divides the interior of the vessel 4 into an upper urine receiving chamber 41 and a lower urine measuring chamber 42. The jet 5 strikes the disc 6, whereby the vertical flow constituted by the jet is deflected to a substantially horizontal flow prior to the supply of the liquid to the lower urine measuring chamber 42 of the vessel 4 and, in applicable cases, of liquid 8 in the vessel. The disc 6 is capable of rotation at high speed, so that the horizontal flow rate of the liquid after the deflection of the flow is high.

According to a preferred embodiment, the disc 6 has a hydrophobic coating to ease the flow of liquid therefrom.

The vessel 4 is preferably substantially cylindrical and designed so that its bottom 9 includes a central hole 10, from which a flange 11 projects upward to a height intended at measurement not to be exceeded by the liquid level in the vessel 4. An axle 12 for driving the disc 6 extends through the hole 10.

Figure 6:
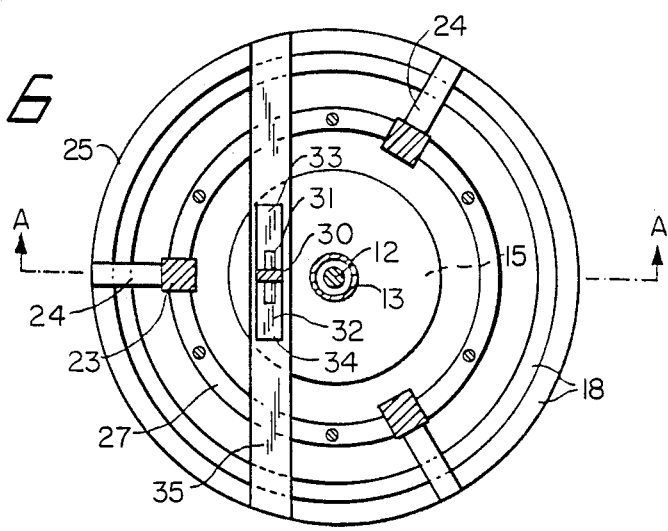
FIG. 6 is a section B—B according to FIG. 5.

In the embodiment of a flow meter according to the invention shown in FIGS. 5 and 6, the collecting part of the meter is designed substantially as in FIG. 4. The axle 12 is mounted in a pipe 13 by bearings 14 and extends to a motor 15 located beneath the vessel on a bottom plate 16, which via a cellular rubber disc 17 is resiliently, elastically attached to the relatively heavy chassis 18 of the meter in order to minimize the transfer of vibrations from the motor 15 and rotating disc 6 to the chassis 18. In the embodiment shown, the chassis 18 comprises a circular bottom 19 and a wall arrangement 20 projecting in a cylindric configuration from the bottom 19. 21 designates a vertically movable thin metal plate, on which the vessel 4 is placed and via which the vertical force from the vessel 4 is intended to be taken up. The plate 21 includes a central hole 22 for extending the pipe 13 and axle 12 therethrough. The plate 21 is resiliently supported via intermediate members in the form of metal blocks 23 on the chassis 18 by means of three upper soft springs 24, which extend radially inward from the circumference 25 of the upper portion of the chassis, and by means of six rods 26 extending from the plate 21 vertically downward at a ring 27, which connects the rods 26 and is resiliently attached also to the lower portion of the chassis by three soft springs 28. The plate 21 hereby is fixed horizontally.

The plate 21 has on its lower surface 29 a cam 30, on which the plate in the embodiment shown is intended to rest and thereby to affect a piezoelectric ceramic crystal 31. According to a preferred embodiment, the crystal has a length of 20 mm and is of the type marketed under the designation PXE 5, multimorph, Philips. The crystal is longitudinally and symmetrically glued on the upper surface of a spring 32 which is 60 mm long, 10 mm wide and 1 mm thick.

The spring is rigidly clamped at both its ends 33,34 to a beam 35 and, respectively, resting freely on an edge (not shown). The said cam 30 extends diametrically in the chassis, and the beam 35 with the spring 32 and crystal 31 are arranged as a chord perpendicular to the cam, as shown in FIG. 6.

According to a preferred embodiment, beneath the disc 6 a disc 36 supported by the outer pipe 13 is provided with discs 37 intended to brake air movements induced by the rotation of said disc 6.

According also to a preferred embodiment, discs or the like (not shown) are provided at the bottom of the vessel 4 for braking movements of the liquid collected in the vessel.

The method and the way of operation of the arrangement according to the invention substantially should have become apparent from the aforesaid.

The reaction force from the impulse of the jet 5, thus, is absorbed by the rapidly rotating disc 6 free from the vessel 4. The jet is deflected by the disc, and the liquid flow is accelerated to a horizontal speed $v_1$, FIG. 4, at the circumference of the disc. When the liquid meets the wall of the collecting vessel, a horizontal force is obtained which, however, is distributed uniformly over the inner surface of the vessel. By the design described for sensing the force, the force is sensed only in vertical direction. The flow meter, therefore, is not sensitive to the horizontal force. After having met the inner surface 7 of the vessel, the liquid moves slowly with the speed $v_2$ downward along the vessel wall, and as $m_2 dv_2/dt \ll m_2 g$ only a force contribution is recorded which corresponds to $m_2 g$. The resulting force, therefore, with the designations according to FIG. 4 is $$F = (m_o + m + m_2)g \tag{3}$$

$$\text{As } m + m_2 = p \int_0^t Q dt \tag{4}$$

the first derivative of the force becomes $$\frac{dF}{dt} = pgQ \tag{5}$$

Under the above assumptions, thus, the first derivative of the force signal is proportional to the volume flow Q and independent of the flow rate v and its derivative (see equation (2)).

The signal voltage emitted by the piezoelectric crystal arranged in the way described above is directly proportional to the derivative of the applied force. The arrangement described for measuring the force, therefore, eliminates the problems involved with electric derivation.

By means of the design described, comprising upper and lower springs and rods for suspending the plate 21, a stable anchoring of the plate is obtained, so that movement is permitted only in vertical direction, and as mentioned the output signal from the crystal in principle is independent of horizontal forces. Vibrations of the chassis due to movements of the motor can give rise to an interference signal, because the collecting vessel and plate 21 and the attachment constitute a seismic transmitter. This interference has been minimized due to small mass of the vessel/plate and rigid force transmitter.

By means of said discs for braking air movements and liquid movements the size of interference signals has been reduced still more.

As should be obvious from the aforesaid, the invention offers essential advantages over the known art. By means of the disc 6 interferences as a result of the jet meeting directly the vessel are eliminated. The effect of both impulse and wave formation is eliminated. Due to the rapid rotation of the disc, the liquid arrives very rapidly at the collecting vessel wall after the jet has met the disc, and thereby the meter is insensitive to the place where the jet meets the disc. The output signal. therefore, is not interfered by oscillating movement of the jet, as shown in FIG. 3.

Figure 8:
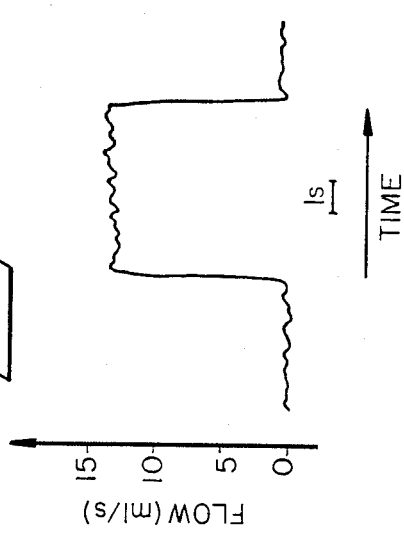
FIG. 8 shows the response on an applied pulse shape flow at a flow meter according to the invention.
Figure 5:
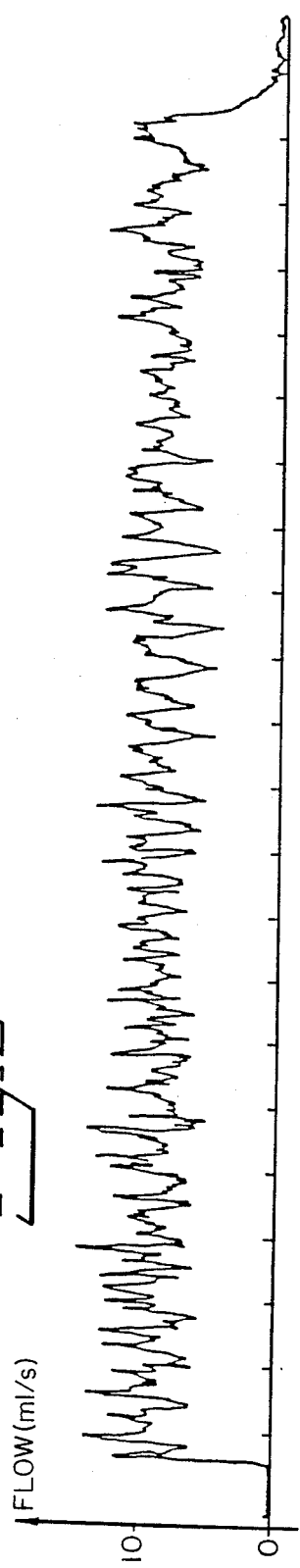
Figure 7:
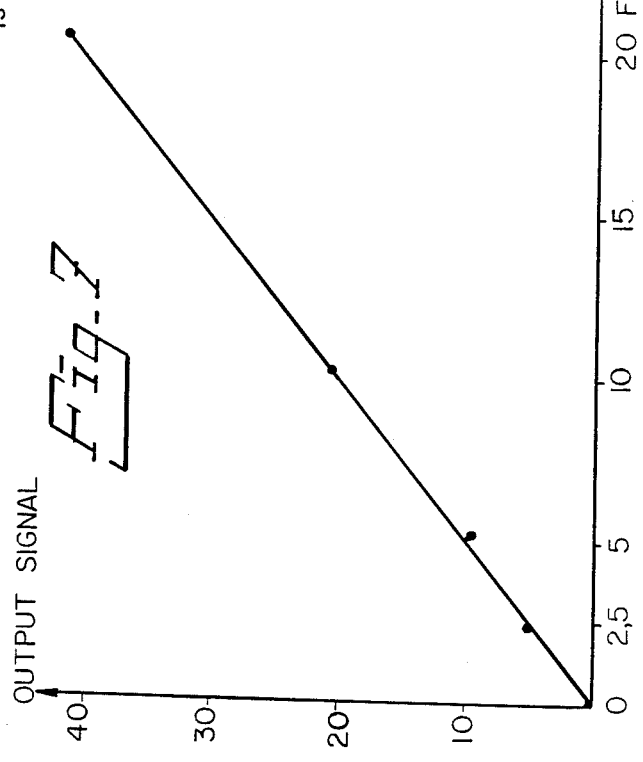
FIG. 7 shows an electric output signal as a function of applied constant flow at a flow meter according to the invention.

In FIGS. 7 and 8 measurement results obtained with a flow meter according to the invention are shown. They show a linear relation between applied flow and output signal. The response to applied pulse shape flow is rapid and does not show overshoots. When the pulse shape flow is recorded with an electric time constant of 0.1 sec.. a response time is obtained which from the start of the flow to its arrival at 63% of the final value is about 0.2 sec.

The invention has been described above with reference to substantially one embodiment. Several more embodiments and minor alterations, of course, can be imagined without therefore abandoning the invention idea.

Other configurations of the rotating member 6 than the disc shape shown, for example, can be imagined. In FIG. 5 a central cone-shaped portion is shown. The rotating member, however, can be designed so that the cone shape entirely dominates.

We claim:

1. A method for measuring the rate at which urine is emitted without interference from the impulse force of the urine stream comprising:
   collecting urine in the form of a free-falling stream in a collecting vessel having substantially vertical walls;
   deflecting the free-flowing stream of urine using a rotating device contained within the collecting vessel but mounted separately therefrom, said device being rotated at a speed sufficient to generate a centrifugal force such that the vertical velocity of the urine is converted into horizontal velocity;
   causing the deflected urine stream to flow downward from the rotating device into a measuring chamber, said chamber being equipped with means for measuring the amount of urine contained in said measuring chamber;
   determining the rate of change of said amount of urine in the measuring chamber, whereby the rate of urine emission can be accurately measured without interference from the impulse force of the urine stream.

2. A method as defined in claim 1, further comprising the step of weighing the collecting vessel by means of a vetically moveable disc on which the vessel is supported, which disc is operably connected to means which measures the rate of change of said weight.

3. A method as defined in claim 2, further comprising the step of generating a signal voltage from the means for measuring the rate of change in weight, wherein the signal voltage is directly proportional to the time derivative of force.

4. A method according to claim 2, further comprising the step of generating an output signal from a piezoelectric crystal proportional to the rate of change of said weight, wherein said disc via a cam affects the piezoelectric crystal which is attached to a spring, which is clamped at both ends and, respectively, freely supported.

5. A method as defined in claim 1, further comprising the step of braking air movement induced by rotation of said device using discs provided below said device.

6. An apparatus for measuring the rate at which urine is emitted without interference from the impulse force of the urine stream comprising:
   a collecting vessel for receiving urine in the form of a free-falling stream, said vessel having a base and generally cylindrical vertical walls;
   mounting means to support the weight of the vessel and urine collected therein;
   a rotatable device positioned within the vessel such that after entering the collecting vessel, the free-falling stream of urine will strike the rotatable device, said rotatable device having an outer edge substantially adjacent to but not touching the interior of said vertical walls of the vessel, and said rotatable device dividing the vessel into an upper urine receiving chamber and a lower urine measuring chamber;
   means for rotating the rotatable device at a rate sufficient to cause the free-falling stream of urine striking the rotatable device to be deflected toward the vertical walls such that the vertical velocity of the urine stream is converted to horizontal velocity; and
   means for measuring the weight of the vessel and the urine collected in the urine measuring chamber, and determining therefrom the rate of urine emission, wherein the rotatable device is mounted separately from the collecting vessel such that neither the rate of rotation of the device nor the impulse force of the free-falling stream of urine contributes to the measured weight of the urine collected.

7. An apparatus as defined in claim 6, further comprising a vertically movable plate on which the weight of the collecting vessel is taken up, means for measuring the rate change of said weight and a heavy chassis on which said plate and means are mounted.

8. An apparatus as defined in claim 7, characterized in that the rotatable device is operably connected to a motor located on a bottom plate, which via a cellular rubber plate is resiliently attached to the heavy chassis of the apparatus.

9. An apparatus as defined in claim 7, characterized in that said plate via intermediate member is attached resiliently to said chassis by means of upper springs and by means of rods extending vertically downward from the plate via a ring connecting the rods and attached to the chassis also by lower springs.

10. An apparatus as defined in claim 6, characterized in that it includes means for emitting a signal voltage which is directly proportional to the rate of change of the weight of said vessel.

11. An apparatus as defined in claim 6 further comprising a cam and a piezoelectric means, said cam being mounted to transmit force from said disc to said piezoelectric means, and said piezoelectric means being attached to a spring which is clamped at both ends and, respectively, freely supported.

12. An apparatus as defined in claim 6, wherein the base of said vessel includes a central hole, from which a flange projects upward to a height intended at measurement not to be exceeded by the liquid level in the vessel, through which hole an axle extends for driving said rotary device.

13. An apparatus as defined in claim 6, further comprising free standing rigidly attached discs located below said rotary device and intended to brake air movements induced by the rotation of said device.

14. An apparatus as defined in claim 6 wherein said rotary device has an upper surface that is at least partially conical.

15. An apparatus as defined in claim 6 characterized in that said rotary device has a hydrophobic surface.

* * * * *

UNITED STATES PATENT AND TRADEMARK OFFICE
CERTIFICATE OF CORRECTION

PATENT NO. : 4,732,160
DATED : MARCH 22, 1988
INVENTOR(S) : ASK ET AL.

It is certified that error appears in the above-identified patent and that said Letters Patent is hereby corrected as shown below:

Column 1, line 50, "uring" should read --urine--;

Column 1, line 54, "valves" should read --values--;

Column 2, line 41, "wall" should read --walls--;

Column 2, line 53, "FIG. 1." should read --FIG. 1, respectively,--;

Column 2, line 54, after "FIG. 3" delete "respectively,";

Column 5, line 63, "vetically" should read --vertically--;

Column 6, line 56, "member" should read --members--.

Signed and Sealed this

Twentieth Day of December, 1988

Attest:

DONALD J. QUIGG

*Attesting Officer*   *Commissioner of Patents and Trademarks*